United States Patent [19]
Greenwald et al.

[11] Patent Number: 6,111,107
[45] Date of Patent: Aug. 29, 2000

[54] HIGH YIELD METHOD FOR STEREOSELECTIVE ACYLATION OF TERTIARY ALCOHOLS

[75] Inventors: Richard B. Greenwald, Somerset; Annapurna Pendri, Matawan; Hong Zhao, Piscataway, all of N.J.

[73] Assignee: Enzon, Inc., Piscataway, N.J.

[21] Appl. No.: 08/974,909

[22] Filed: Nov. 20, 1997

[51] Int. Cl.$^7$ .................................................. C07D 305/14
[52] U.S. Cl. ................................................................. 546/48
[58] Field of Search ...................................... 546/48

[56] References Cited

U.S. PATENT DOCUMENTS

| | | |
|---|---|---|
| 4,943,579 | 7/1990 | Vishnovajjala et al. ............... 546/48 |
| 5,614,549 | 3/1997 | Greenwald et al. .................. 546/48 |
| 5,646,159 | 7/1997 | Wall .................................... 546/48 |
| 5,840,900 | 11/1998 | Greenwald et al. ................. 546/48 |
| 5,880,131 | 3/1999 | Greenwald ......................... 514/279 |

OTHER PUBLICATIONS

Greenwald, Tetrahedron: Asymettry vol. 9 pp.915–918, Mar. 1998.

Scriven, Eric F.V., 4–Dialkylaminopyridines: Super Acylation and Alkylation Catalysts, Chem. Soc. Rev.; pp. 129–161; 1983.

Csanady, G. et al., A Convenient Synthesis of t–Butyl Esters of Amino Acids, OPPI Briefs vol. 20, No. 2; pp. 180–184; 1988.

Chevallet, Pierre, et al. Facile Synthesis of Tert–Butyl Ester of N–Protected Amino Acids with Tert–Butyl Bromide, Tetrahedron Letters, vol. 34, No. 46; pp. 7409–7412; 1993.

Gibson, F. S., et al. Bis [[4–(2,2–dimethyl–1,3–dioxolyl)]methyl]–carbodiimide (BDDC) and Its Application to Residue–Free . . . , J. Org. Chem., vol. 59 pp. 7503–7507; 1994.

Ishihara, K., et al. Scandium Trifluoromethanesulfonate as an Extremely Active Acylation Catalyst, J. Am. Chem. Soc, vol. 117, pp. 4413–4414; 1995.

Fukuzawa, S., et al., Direct Synthesis of Chiral Acetals from Carbonyl Compounds and Chiral Diols:Sequentional One–Pot Asymmetric Silylcyanation Reaction Catalyzed by Scandium(III) Triflate SYNLETT, pp. 1077–1078; 1995.

Ishihara, K., et al., Scandium Trifluoromethanesulfonate as an Extremely Active Lewis Acid Catalyst in Acylation of Alcohols with Acid Anhydrides and Mixed Anhydrides, J. Org.Chem., vol. 61, pp. 4560–4567; 1996.

Ishihara, K., et al., Scandium Trifluoromethanesulfonimide and Scandium Trifluoromethanesulfonate as Extremely Active Acetalization Cataylsts, SYNLETT, pp. 839–841; 1996.

El Gihani, M., et al. Scandium and Copper Triflate–Catalysed Acylaminoalkylation and Friedel–Crafts Alkylation Reactions, SYNLETT, pp. 871–872; 1996.

Saito, T., et al., Ytterbium Triflate–Catalyzed Asymmetric Hetero Diels–Alder Cyclo–addition of a . . . , Tetrahedron Letters, vol. 38, No. 18, pp. 3231–3234; 1997.

*Primary Examiner*—Richard L. Raymond
*Assistant Examiner*—Deepak Rao
*Attorney, Agent, or Firm*—Roberts & Mercanti, LLP

[57] ABSTRACT

The present invention is directed to methods of forming esters of tertiary alcohols. The methods include reacting a compound containing a tertiary alcohol with an acyl heteroaromatic ion-based compound of the formula:

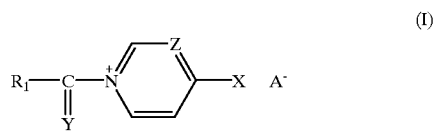

(I)

wherein $R_1$ is an aromatic or aliphatic acid residue;

Y is O or S;

Z is $R_2$ N;

X is selected from the group consisting of

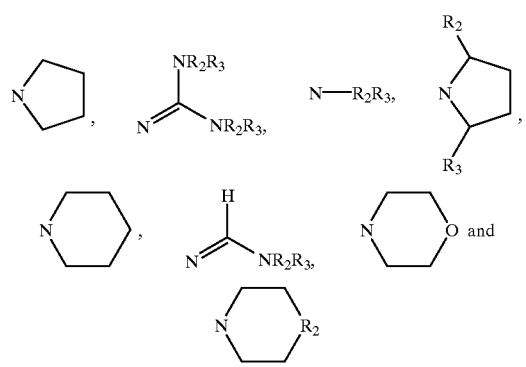

wherein $R_2$ and $R_3$ are independently selected from the group consisting of H, $C_{1-6}$ alkyls, $C_{1-6}$ substituted alkyls, $C_{1-6}$ heteroalkyls, $C_{3-8}$ branched alkyls, $C_{3-8}$ cycloalkyls, $C_{1-6}$ substituted heteroalkyls, aryls, substituted aryls, except that $R_2$ is not H when X is

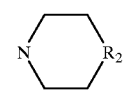

$C_{1-6}$ alkyl aralkyls, $C_{1-6}$ heteroalkyl aralkyls, $C_{3-8}$, branched alkyl aralkyls and $C_{3-8}$ cycloalkyl aralkyls; and $R_2'$ is the same as $R_2$ except that $R_2'$ is not H;

in the presence of a lanthanide$^{III}$ metal-based catalyst and a base. In preferred embodiments, a substantially pure optical isomer of a compound containing a tertiary alcohol is used and the resultant esters are of sufficient purity so that expensive and time consuming recrystallization or purification steps are avoided.

37 Claims, 2 Drawing Sheets

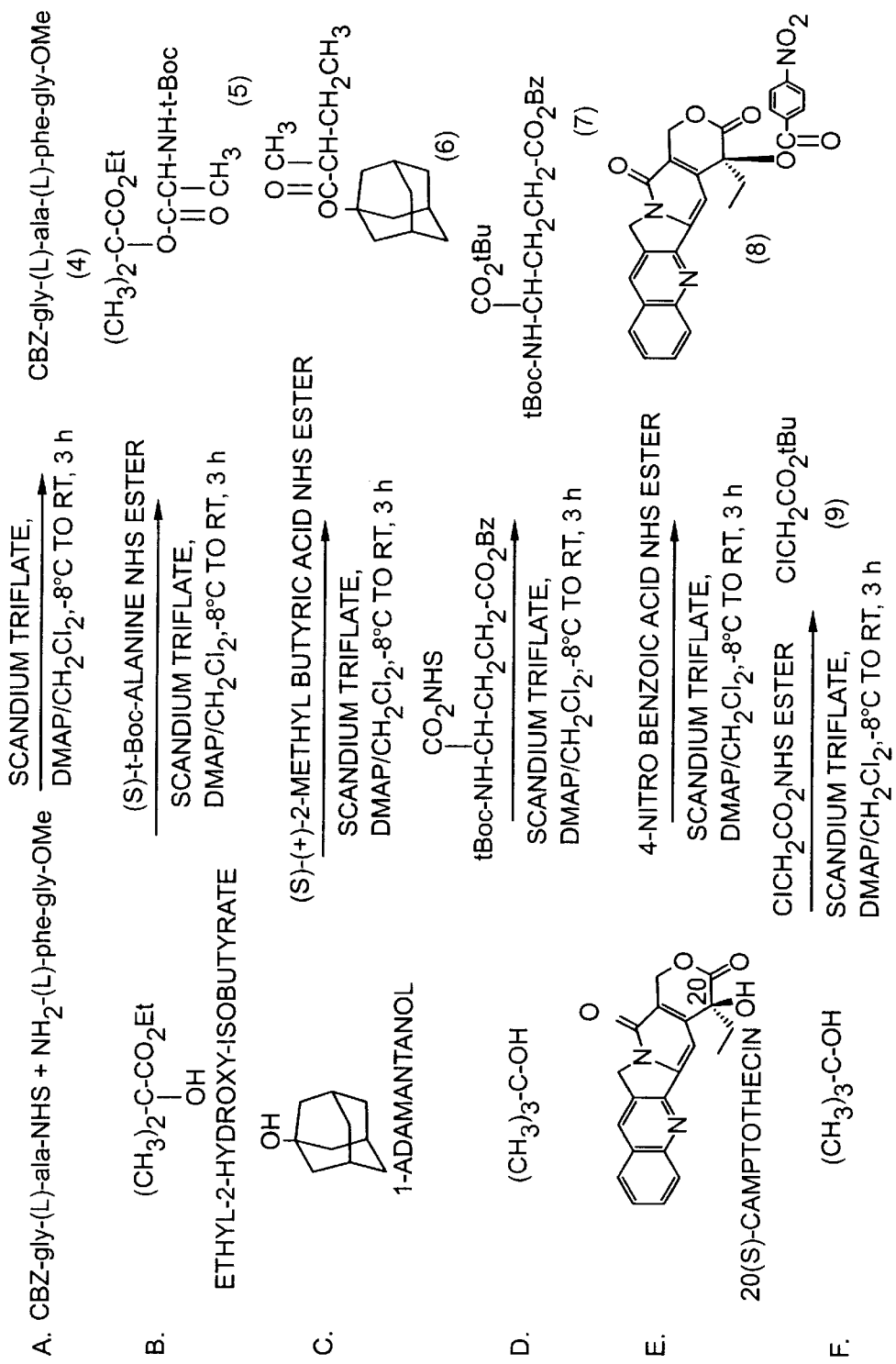

HIGH YIELD METHOD FOR STEREOSELECTIVE ACYLATION OF TERTIARY ALCOHOLS

FIELD OF THE INVENTION

The present invention relates to high yielding methods of acylating tertiary alcohols. In particular, the invention relates to methods of forming esters of tertiary alcohols while maintaining high degrees of sterioselectivity.

BACKGROUND OF THE INVENTION

Over the years, several methods of administering therapeutic substances to mammals have been proposed. Although the oral route of administration is highly desirable from a patient compliance standpoint, the route is not practical for a large number of therapeutic compounds. Consequently, parenteral administration of many compounds via the intravenous or intramuscular route must be employed. Even when these routes are employed, there often problems associated with administration of the medicinal. This is especially true when the compound is either poorly soluble or is rapidly degraded or eliminated in vivo.

As an outgrowth of the above, there has been significant effort directed to developing useful transport mechanisms for effectively delivering therapeutic compounds to patients in need of treatment. More recently, interest has been shown in preparing prodrug-based transport forms in order to solve problems such as poor solubility associated with particular therapeutic compounds. For example, commonly-assigned U.S. Pat. No. 5,880,131 discloses using amino acid spacer groups with poly(ethylene glycol) ester prodrugs of 20-(S)-camptothecin, an anti-cancer alkaloid having a highly hindered OH at the 20-position. Esterification of the 20-OH group was accomplished in high yield by employing diisopropyl carbodiimide (DIPC) in the presence of 4-dimethylaminopyridine (DMAP). The reaction, however, is accompanied by substantial racemization for each stereoisomer, usually about 25% for t-Boc (L)-alanine and about 40% for t-Boc-(D)-alanine. In cases where conservation of chiral purity is necessary or desired, increased costs are incurred by efforts to isolate the desired diasteriomer because the artisan must subject the intermediate to one or more recrystallizations which also drive down the final yield. It would therefore be highly desirable to eliminate crystallization steps, especially if large scale quantities are required.

Recent advances in the acylation of tertiary alcohols which produce high yields of esters employ symmetrical carboxylic acid anhydrides and the readily-available Lewis acid catalyst scandium triflate Sc(OTf)₃. This procedure, however, has been determined to be unsuitable for acylating hindered tertiary alcohols with mixed anhydrides of complex acids. The same authors later reported in Synlett. September 1996, 839-841 that Sc(OTf)₃ and a related catalyst were extremely active acetalization catalysts which afforded highly diastereoselective reactions. No information was provided regarding acylation-type reactions.

Gibson, et al. in J. Org. Chem. 1994, 59, 7503–7507 reported that high yields of t-butyl esters were possible with little or no racemization. However this approach has been deemed to be not convenient by some practitioners because it entails the multi-step synthesis of a water-soluble carbodimide that must be converted to a t-butyl isourea using a cuprous chloride catalyst.

In view of the foregoing, synthesis of esters of tertiary alcohols with complex acids, especially amino acids, while maintaining chirality remains a challenging task. A need exists, therefore, for an improved method of forming esters of tertiary alcohols, especially when stereoselectivity in esterification of compounds containing a tertiary alcohol is required. The present invention addresses this need.

SUMMARY OF THE INVENTION

In one preferred embodiment, the present invention is directed to methods of forming esters of tertiary alcohols. The methods include reacting an acyl heteroaromatic ion compound of the formula:

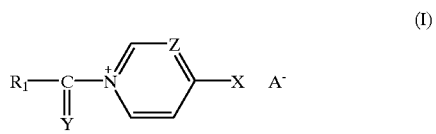

(I)

wherein:

A is an anion;

$R_1$ is an aromatic or aliphatic acid residue;

Y is O or S;

Z is CH or N;

X is selected from the group consisting of

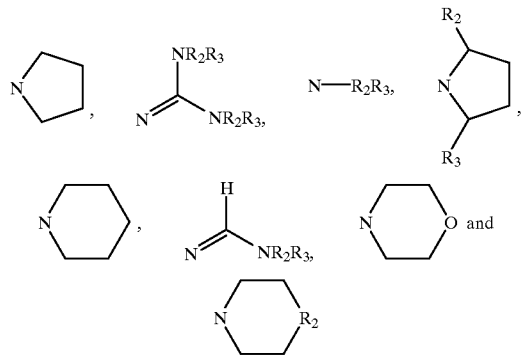

wherein:

$R_2$ and $R_3$ are independently selected from the group consisting of H, $C_{1-6}$ alkyls, $C_{1-6}$ substituted alkyls, $C_{1-6}$ heteroalkyls, $C_{3-8}$ branched alkyls, $C_{3-8}$ cycloalkyls, $C_{1-6}$ substituted heteroalkyls, aryls, substituted aryls, $C_{1-6}$ alkyl aralkyls, $C_{1-6}$ heteroalkyl aralkyls, $C_{3-8}$ branched alkyl aralkyls and $C_{3-8}$ cycloalkyl aralkyls;

and $R_2'$ is the same as $R_2$ except that $R_2'$ is not H; with a compound containing a tertiary alcohol in the presence of a lanthanide[III] metal-based catalyst and a base.

The acyl heteroaromatic-ion based compound can be formed by either 1) reacting a carboxylic acid derivative with a condensing agent and a heteroaromatic-based catalyst of Formula (II):

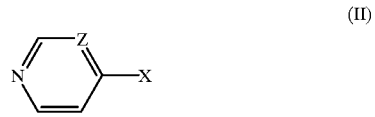

(II)

where X and Z are defined as above with regard to Formula (I); or 2) reacting an acylating agent such as a mixed anhydride, N-hydroxy-succinimide ester or other active ester of a carboxylic acid or an acid halide with a heteroaromatic-based catalyst of Formula (II).

Preferred lanthanide$^{III}$ metal-based catalysts are scandium-based catalysts such as scandium triflate (scandium trifluoromethanesulfonate) and scandium trifluoromethanesulfonimide. Preferred bases include dimethylaminopyridine (DMAP) or diethylaminopyridine.

In other aspects of the invention the above methods are modified by using chiral compounds containing a tertiary alcohol and/or chiral acyl heteroaromatic ion-based compounds in order to produce high yields of essentially pure enantiomeric products. For example, a compound containing a tertiary alcohol can be reacted with a substantially pure isomer of a compound of Formula (I), i.e. an acyl heteroaromatic ion-based compound, and substantially maintain the chirality in the resultant ester of the tertiary alcohol.

As a result of the present invention, substantially single diastereomeric esters of compounds containing a tertiary alcohol are formed. The reactions are carried out under relatively mild conditions and maintain about 90%, and preferably up to about 95% diastereoselectivity when substantially pure optical isomers are used.

The esters of tertiary alcohols formed as a result of the invention have wide applicability. For example, they are especially useful in the field of pharmaceutical chemistry. The high degree of diasterioselectivity allows the artisan to make useful chiral prodrug intermediates in high optical purity and high isolated yield. For example, stereoselective esterification of compounds such as 20-S-camptothecin and derivatives thereof is readily accomplished in high yield and with substantially complete conservation of the chirality (i.e. >97% pure diasteriomer). The small amounts of undesired diastereomeric impurity which may be generated with the methods of the present invention can be removed via crystallization with minimal effect on the overall yield. Therefore, the time and expense of the recrystallization processes which were heretofore required to raise the optical purity of the desired intermediate is minimized or avoided.

BRIEF DESCRIPTION OF THE DRAWINGS

FIG. 2 illustrates reaction schemes for the compounds prepared in Examples 8–12.

DETAILED DESCRIPTION OF THE INVENTION

Figure 1:
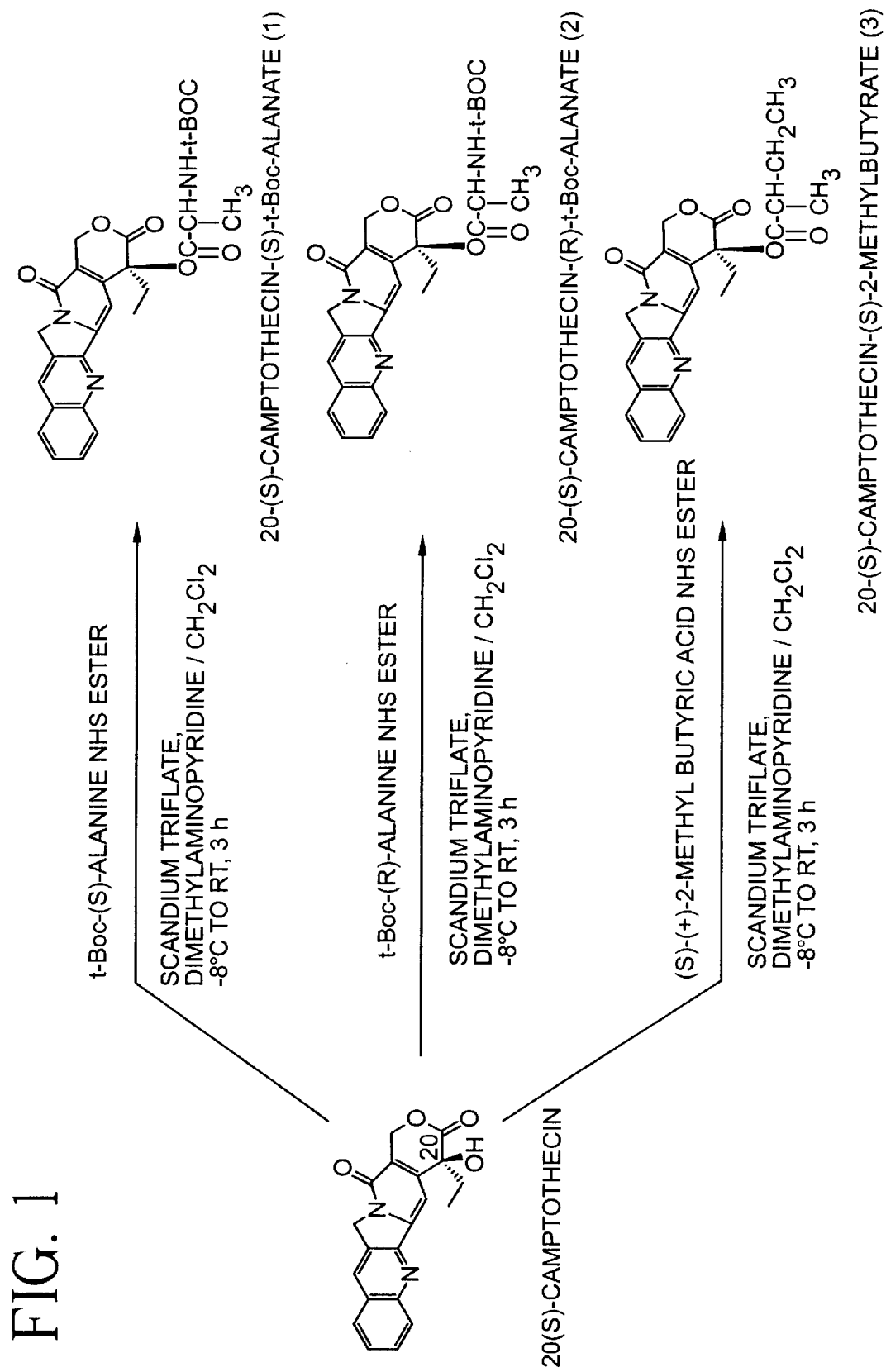
FIG. 1 illustrates reaction schemes for the compounds prepared in Examples 1–7.

In one aspect of the invention there is provided methods of forming esters of tertiary alcohols. The methods include reacting an acyl heteroaromatic ion-based compound of the formula:

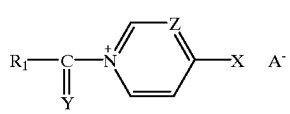

(I)

wherein:

A is an anion;

$R_1$ is an aromatic or aliphatic acid residue;

Y is O or S;

Z is CH or N; and

X is selected from the group consisting of

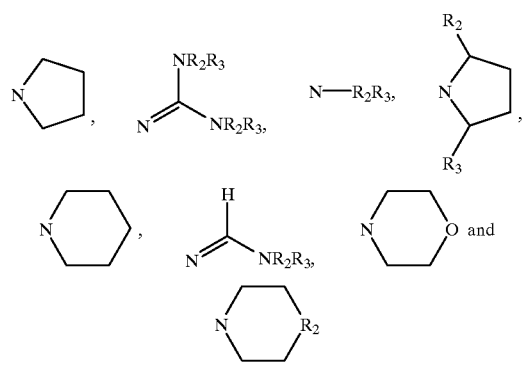

wherein:

$R_2$ and $R_3$ are independently selected from the group consisting of H, $C_{1-6}$ alkyls, $C_{1-6}$ substituted alkyls, $C_{1-6}$ heteroalkyls, $C_{3-8}$ branched alkyls, $C_{3-8}$ cycloalkyls, $C_{1-6}$ substituted heteroalkyls, aryls, substituted aryls, $C_{1-6}$ alkyl aralkyls, $C_{1-6}$ heteroalkyl aralkyls, $C_{3-8}$ branched alkyl aralkyls and $C_{3-8}$ cycloalkyl aralkyls; and $R_2'$ is $R_2$ except that $R_2'$ is not H;

with a compound containing a tertiary alcohol in the presence of a lanthanide$^{III}$ metal-based catalyst and a base.

Suitable anions for (A) include negative ion-conferring moieties which are necessary to balance the charge of the acyl heteroaromatic ion, such as chloride, fluoride, bromide, iodide, N-hydroxysuccinimide, etc.

Examples of suitable $R_1$ moieties include the aromatic and aliphatic residues of the aromatic and aliphatic carboxylic acids described below. For example, aromatic residues include phenyl, naphthyl, thienyl, etc., and aliphatic residues include alkyl, branched alkyl, substituted alkyls such as benzyl, heteroalkyls, cycloalkyls, amino acid residues, etc.

Formation of Acyl Heteroamatic Ion based Compound

A key to maintaining the chiral purity of the esters formed as a result of the present invention is the formation of an acyl heteroaromatic-ion based intermediate compound, designated herein as Formula (I). While Applicants are not bound by theory, it is believed that the lanthanide$^{III}$ metal-based catalyst coordinates with the acyl heteroaromatic-ion based compound producing a highly reactive species. Subsequently, acylation of the tertiary alcohol occurs so rapidly that racemization of chiral intermediates is substantially precluded.

In one aspect of the invention, the acyl heteroaromatic-ion based intermediate compound can be prepared by reacting an acylating agent with a compound of the formula:

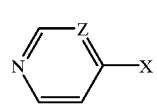

(II)

wherein

Z is CH or N; and

X is selected from the group consisting of

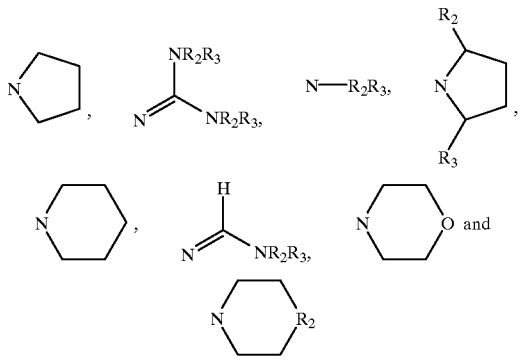

wherein:

R$_2$ and R$_3$ are independently selected from the group consisting of H, C$_{1-6}$ alkyls, C$_{1-6}$ substituted alkyls, C$_{1-6}$ heteroalkyls, C$_{3-8}$ branched alkyls, C$_{3-8}$ cycloalkyls, C$_{1-6}$ substituted heteroalkyls, aryls, substituted aryls, C$_{1-6}$ alkyl aralkyls, C$_{1-6}$ heteroalkyl aralkyls, C$_{3-8}$ branched alkyl aralkyls and C$_{3-8}$ cycloalkyl aralkyls; and R$_2$' is the same as R$_2$ except that R$_2$' is not H.

Preferably, (Z) is CH and (X) is NR$_2$R$_3$, where R$_2$ and R$_3$ are both alkyls, and more preferably both methyl. Thus, particularly preferred compounds of Formula (II) are 4-dialkylaminopyridines such as dimethylaminopyridine (DMAP). These acylation catalysts are readily prepared from suitable 4-substituted pyridines. See, for example, "4-Dialkylaminopyridines: Super Acylation and Alkylation Catalysts" *Chem. Soc. Rev.* (1983)129–161, the contents of which are incorporated herein by reference.

The acylating agents which are useful in the formation of the intermediate compound of Formula (I) can be selected from among mixed anhydrides, cyclic anhydrides, N-hydroxysuccinimide esters, N-hydroxyphthlimide esters, active esters of carboxylic acids and acid halides. Additionally, as described in more detail below, the free acid can be used in the presence of a coupling reagent such as dialkylcarbodiimides, EEDQ, Mukaiyama-type reagents, and the like which form activated acyl intermediates in situ.

In those aspects of the invention where the acylating agent is an active ester of a carboxylic acid, aliphatic and aromatic active esters of carboxylic acids can be used.

Aliphatic active esters of carboxylic acid derivatives include, without limitation:

a) N-hydroxysuccinimide (NHS), N-hydroxybenzotriazole, N-hydroxyphthalimide, N-hydroxyazabenzotriazole and benzotriazol-1-yloxy-tris(dimethylamino) phosphonium hexaflurorphosphate, (BOP reagent);

b) blocked amino acid active esters such as NHS orp-nitrophenyl (PNP) esters of S- and R-forms of alanine, which are preferred, leucine, isoleucine, phenylalanine, tryptophan, methionine and proline;

c) S- and R-forms of 2-chloropropionic acid, 2-methylbutyric acid and other substantially pure optical isomers of aliphatic active esters of carboxylic acid compounds; and d) non-chiral active esters.

Aromatic active esters of carboxylic acid compounds can be selected from, for example, benzoic acid derivatives such as 4-nitro-benzoic acid, naphthoic active esters and substituted heteroaromatic active esters such as nicotinic acid active esters.

In those aspects of the invention where the acylating agent is a mixed anhydride, suitable examples of mixed anhydrides include C$_{1-2}$ alkyl trifluoromethyl anhydrides, alkyl p-nitrophenyl ahydrides.

Still further examples of suitable acylating agents include N-hydroxy-succinimide esters, N-hydroxyphthalimide esters and acid halides such as acid bromides, acid chlorides, acid fluorides and acid iodides.

In another aspect of the invention the acyl heteroaromatic-ion based compounds corresponding to Formula (I) are prepared by reacting a carboxylic acid derivative of the Formula (III): R$_4$CO$_2$H where R$_4$ is selected from the group consisting of C$_{1-40}$ alkyls, C$_{1-40}$ substituted alkyls, C$_{1-20}$ heteroalkyls, C$_{3-20}$ branched alkyls, C$_{3-12}$ cycloalkyls, C$_{1-20}$ substituted heteroalkyls, aryls, substituted aryls, C$_{1-12}$ alkyl aralkyls, C$_{1-12}$ heteroalkyl aralkyls, C$_{3-20}$ branched alkyl aralkyls and C$_{3-12}$ cycloalkyl aralkyls;

with a condensing agent in the presence of a heteroaromatic base such as DMAP. This method allows the activated acyl heteroaromatic intermediate to be formed in situ.

The condensing agent can be selected from compounds such as 1,3-diisopropylcarbodiimide (DIPC), 1,(3-dimethyl aminopropyl) 3-ethyl carbodiimide (EDC), dialkyl carbodiimide, Mukaiyama reagents, (e.g. 2-halo-1-alkyl-pyridinium halides) or propane phosphonic acid cyclic anhydride (PPACA), N-ethoxycarbonyl-2-ethoxy- 1,2-dihydroquinoline (EEDQ), dicyclohexylcarbodiimide (DCC), etc.

The reactions for forming the intermediate of Formula (1) are preferably carried out in the presence of a base. A non-limiting list of suitable bases include tertiary amine bases including dialkylaminopyridines such as dimethylaminopyridine (D)MAP) and diethylaminopyridine.

Tertiary Alcohol-Containing Compounds

Compounds which contain a tertiary alcohol can be selected from a wide variety of therapeutic and otherwise useful materials. For example, in one preferred aspect of the invention compounds such as camptothecin and camptothecin derivatives such as 7-, and/or 9-, and/or 10- and/or 11- substituted camptothecins are selected. Camptothecin is a water-insoluble cytotoxic alkaloid produced by *Camptotheca accuminata* trees indigenous to China and *Nothapodtes foetida* trees indigenous to India. Camptothecin and related compounds and analogs are also known to be potential anticancer or antitumor agents and have been shown to exhibit these activities in vitro and in vivo in laboratory animals.

Camptothecin and certain related analogues share the structure:

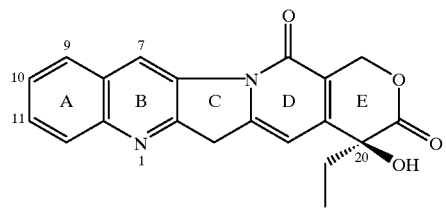

From this core structure, several known analogs have been prepared. For example, the A ring in either or both of the 10- and 11-positions can be substituted with an OH. The A ring can also be substituted with a straight or branched C$_{1-30}$ alkyl or C$_{1-17}$alkoxy, optionally linked to the ring by a heteroatom i.e.- O or S. The B ring can be substituted in the 7-position with a straight or branched $C_{1-30}$ alkyl, $C_{5-8}$ cycloakyl, $C_{1-30}$ alkoxy, phenyl alkyl, etc., alkyl carbamate, alkyl carbazides, phenyl hydrazine derivatives, etc. Other substitutions are possible in the C, D and E rings. See, for example, U.S. Pat. Nos. 5,004,758, 4,943,579 and Re 32,518, the contents of which are incorporated herein by reference. Some preferred camptothecin derivatives for use herein include the 9-acetyl-camptothecin, 9-amino-camptothecin, 10-hydroxycamptothecin such as topotecan, 11-hydroxy-camptothecin and/or the 10,11-dihydroxycamptothecin derivatives. As the artisan will appreciate, the 10-hydroxycamptothecin, 11-hydroxycamptothecin and the 10,11-dihydroxycamtothecin analogs occur naturally as one of the minor components in C. Acuminata and its relatives. Additional substitutions to these compounds, i.e. 7-alkyl-, 7-substituted alkyl-, 7-amino-, 7-aminoalkyl-, 7-aralkyl-, 9-alkyl-, 9-amino, 9-aralkyl- camptothecin etc. derviatives can be made using known synthetic techniques without undue experimentation. Under the conditions described herein, acylation takes place at the 20-OH. Structurally, these compounds are shown below.

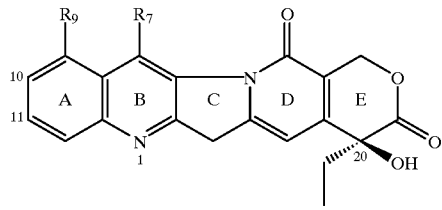

In the structure shown above, $R_9$ can be, for example, one of Ac, $NO_2$, $NH_2$, $N_3$, hydrogen, halogen (F, Cl, Br, I), COOH, OH, O—$C_{1-8}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl), O—, NH— and S—$CH_2CH_2N$ $(CH_2CH_2OH)_2$, O—, NH— and S— $CH_2CH_2CH_2N$ $(CH_2CH_2OH)_2$, O—, NH— and S—$CH_2CH_2N$ $(CH_2CH_2CH_2OH)_2$, O—, NH— and S—$CH_2CH_2CH_2N$ $(CH_2CH_2CH_2OH_2)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl.

Preferred compounds are those in which $R_9$ is H, Ac, halogen, nitro or amino.

$R_7$ in the structure shown above is H, $C_{1-8}$ alkyl, or $CH_2NR_{10}R_{11}$ where (a) $R_{10}$ and $R_{11}$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl;

(b) $R_{10}$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy, $C_{1-6}$ alkyl, $C_{1-6}$ alkoxy or $C_{1-4}$, alkoxy-$C_{1-6}$ alkyl and $R_{11}$ is —$COR_{12}$ where $R_{12}$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl; or (c) $R_{10}$ and $R_{11}$ taken together with the nitrogen atom to which they are attached form a saturated 3–7 membered heterocyclic ring which may contain a O, S or $NR_{12}$ group, where $R_{12}$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and -$COR_{13}$ where $R_{13}$ is hydrogen, $C_{1-6}$ alkyl perhalo-$C_{1-6}$ alkyl, $C_{1-6}$ alkoxy, aryl, and aryl substituted with one or more of $C_{1-6}$ alkyl, perhalo-$C_{1-6}$ alkyl, hydroxy-$C_{1-6}$ alkyl, or $C_{1-6}$ alkoxy-$C_{1-6}$ alkyl groups.

Preferred aryl groups are phenyl and naphthyl. Suitable heterocyclic rings when $R_9$ and $R_{10}$ are taken together with the nitrogen atom to which they are attached include: aziridine, azetidine, pyrrolidine, piperidine, hexamethylenimine, imidazolidine, pyrazolidine, isoxazolidine, piperazine, N-methylpiperazine, tetrahydroazepine, N-methyl-tetrahydroazepine, thiazolidine, etc.

Other tertiary OH-containing compounds include t-butanol, 1-adamantanol, ethyl-2-hydroxy-isobutyrate, prostaglandin analogs, vitamin $D_3$ metabolites as described by Ting Chen et al, Journal of Organic Chemistry, Vol 62(13) 4349–57, the disclosure of which is incorporated herein by reference and natural products containing tertiary alcohols such as frontalin.

As can be seen from the above, not all of the esters of compounds containing a tertiary alcohol are "biologically active". Some compounds are useful as intermediates or have (chemical) utility as the ester.

In accordance with the present invention, the nucleophile, having an available chiral tertiary hydroxyl moiety, is capable of undergoing a substitution reaction with a chiral intermediate of Formula (I) in the presence of a lanthanide$^{III}$ metal-based catalyst and a sufficient amount of a dialkylaminopyridine base, typically an excess, in order to form an ester of the tertiary alcohol, including, in some aspects, substantially a single diastereomeric ester.

The Lanthanide Metal-based Catalysts

Suitable lanthanide$^{III}$ metal-based catalysts include those based on lanthanum, cerium, praseodymium, samarium, europium, gadolinium, terbium, dysprosium, holmium, erbium, thulium, ytterbium and lutetium. Preferably, the lanthanide$^{III}$ metal-based catalyst is a scandium$^{III}$-based catalyst such as a scandium perhaloalkylsulfonate. The alkyl portion of the perhaloalkylsulfonate can be a methyl, ethyl, butyl or other lower alkyl, substituted alkyl, etc. The halo portion of the perhaloalkylsulfonate is preferably a trifluoromethyl, pentafluorethyl or a moiety of the formula $C_nH_{2n+1}$—$CF_2$—, where (n) is a positive integer. Some particularly preferred scandium-based catalysts for use in the present invention include scandium triflate (scandium trifluoromethanesulfonate) and scandium triflimide (scandium trifluoromethanesulfonimide). The many of these catalysts is available from Aldrich. The others can be made according to techniques found in relevant literature.

The lanthanide$^{III}$ metal-based catalyst will be present in an amount which is sufficient to achieve the desired result, i.e. an amount which is sufficient to catalyze the formation of tertiary alcohols esters, and in some preferred embodiments, catalyze the forming of substantially diastereoseletive esters of compounds containing a tertiary alcohol. Within this framework, the catalyst will be present in an amount of from about 20 to about 100 mol % based on the amount of heteroaromatic ion-based intermediate; preferably in an amount of from about 40 to about 70 mol % and most preferably in an amount of from about 50 to about 60 mol %.

The ratio of the acyl heteroaromatic ion-based compound to the compound containing a tertiary alcohol in the reaction can be from about 5:1 to about 1:5 and is preferably from about 4:1 to about 1:4. The exact ratio of the ingredients will be apparent to the skilled artisan upon selection of the specific tertiary alcohol-containing compound and the particular acyl heteroaromatic ion intermediate formed.

The methods are also preferably carried out in the presence of an organic solvent. A non-limiting list of suitable organic solvents include, without limitation, dichloromethane, chloroform, acetoniltrile, dichloroethane, tetrahydrofuran, dimethylsulfoxide, and toluene.

The reaction temperature can range from a temperature of from about −20° to about 60° C.; preferably from about −15 to about 40° C. and most preferably from about −10 to about 25° C.

Substantially Single Diasteromeric Esters

In another embodiment of the invention, there are provided methods of forming substantially diastereoseletive esters of compounds containing a tertiary alcohol. The methods can be used to substantially maintain diastereoselectivity of the reaction product when a chiral tertiary alcohol and/or a chiral activated carboxylic acid ester or both are used as reactants. For example, a compound containing a tertiary alcohol such as a camptothecin analog is reacted with a substantially pure optical isomer of an acyl heteroaromatic ion-based compound of the formula:

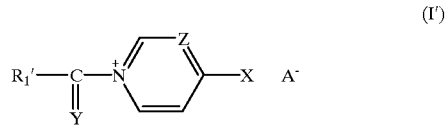

(I')

wherein:

A is an anion;

$R_1'$ is a substantially pure optical isomer of an aromatic or aliphatic acid residue where said residue is as described above with regard to Formula (I);

Y is O or S;

Z is CH or N; and

X is selected from the group consisting of

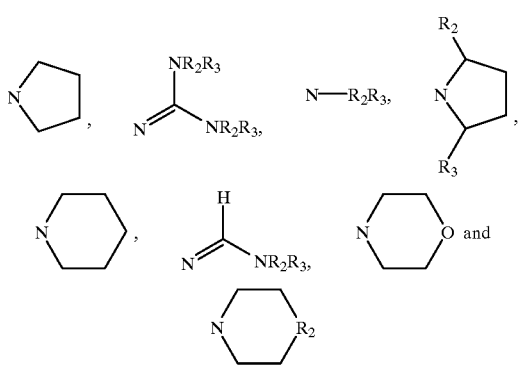

where $R_2$ and $R_3$ are independently selected from the group consisting of H, $C_{1-6}$ alkyls, $C_{1-6}$ substituted alkyls, $C_{1-6}$ heteroalkyls, $C_{3-8}$ branched alkyls, $C_{3-8}$ cycloalkyls, $C_{1-6}$ substituted heteroalkyls, aryls, substituted aryls, $C_{1-6}$ alkyl aralkyls, $C_{1-6}$ heteroalkyl aralkyls, $C_{3-8}$ branched alkyl aralkyls and $C_{3-8}$ cycloalkyl aralkyls; and $R_2'$ is the same as $R_2$ except that $R_2'$ is not H;

in the presence of a lanthanide$^{III}$ metal-based catalyst and a base.

Examples of specific substantially pure optical isomers of the compounds of Formula (I') include $R_1'$=(S) tBoc ala, (R) tboc ala, as well as other blocked chiral amino acids, (S) 2-chloropropionic acid, etc.

The method can also be carried out using either a substantially pure optical isomer of a compound containing a tertiary alcohol and a compound of Formula (I') or using a non-optically active derivative of (I), in combination with the substantially pure optically pure isomer of a non-chiral tertiary alcohol. In either case, the reaction is carried out in the presence of a lanthanide$^{III}$ metal-based catalyst and a sufficient amount of a preferably dialkylaminopyridine base in order to form substantially a single diastereomeric ester of compounds containing a tertiary alcohol. As a result of the processes described herein, the ester maintains at least about 90% diastereoselectivity or optical purity, preferably at least about 95% and most preferably at least about 97% diastereoselectivity or optical purity.

Synthesis of Biologically Active Conjugates

In yet a still further aspect of the invention, methods of preparing prodrug conjugates using the optically pure ester described above are provided. The methods include reacting a substantially pure diastereomeric ester of a tertiary alcohol containing compound (abbreviated below as: "ester of t-OH") with a carboxylic acid derivative of a substantially non-antigenic polymer (SNAP) to form a conjugate having an ester linkage between the polymer and the compound. In accordance therewith, the conjugate is represented below:

SNAP-linkage-(ester of t-OH) or (ester of t-OH)-linkage-(SNAP)-linkage-(ester of t-OH).

The conjugation methods of the present invention can also include reacting the substantially pure diastereomeric ester of the compound containing the tertiary alcohol with a carboxylic acid derivative of a substantially non-antigenic polymer. The carboxylic acid derivatives of the present invention are preferably prepared from poly(alkylene oxides) (PAO's) such as polyethylene glycol which are water soluble at room temperature. See, for example commonly assigned U.S. Pat. No. 5,605,976, the contents of which are incorporated herein by reference, which discloses formation of carboxylic acid derivatives of substantially non-antigenic acids. Within this group are omega-substituted polyalkylene oxide derivatives such as methoxypoly (ethylene glycols) (mPEG-OH). Other suitable alkyl-substituted PAO derivatives include those containing mono-terminal $C_1$–$C_4$ groups. Straight-chained non-antigenic polymers such as monomethyl PEG homopolymers are preferred. Alternative polyalkylene oxides such as other poly(ethylene glycol) homopolymers, other alkyl-poly(ethylene oxide) block copolymers, and copolymers of block copolymers of poly(alkylene oxides) are also useful. The polyalkylene oxides are preferably azeotroped prior to conversion to the carboxylic acid.

The polymers of the present invention have a molecular weight of between about 200 and about 100,000 daltons and preferably between about 2,000 and about 80,000 daltons. Molecular weights of between about 4,000 and about 50,000 daltons, however, are most preferred.

The method of the present invention can also be carried out with alternative polymeric substances such as dextrans or other similar non-immunogenic polymers that are capable of being functionalized or activated as mono- or bis- carboxylic acids. The foregoing is merely illustrative and not intended to restrict the type of non-antigenic polymers suitable for use herein.

EXAMPLES

The following non-limiting examples illustrate certain aspects of the invention. All parts and percentages are by weight unless otherwise noted and all temperatures are in degrees Celsius.

Materials

Methoxypoly(ethylene glycol) (m-PEG-OH) MW 5,000 daltons was obtained from NOF, Inc. (New York); PEG MW 20,000 and 40,000 daltons were obtained from Serva, Inc. The solvents were obtained from Aldrich Chemical of Milwaukee, Wis. NHS esters of amino acids were obtained from either Sigma, Advanced Chemtech or Bachem. Each of the products prepared in Examples 1–12 were confirmed structurally by carbon[13] NMR and proton NMR. Diastereomers were analyzed on a ZORBAX $C_8$ reverse phased column and enantiomers were analyzed using a Phenomenex® Chirex chiral column.

Example 1

Synthesis of camptothecin-20-ester of t-Boc -(S)- alanine (1) using DIPC/DMAP (Comparative)

A suspension of t-Boc -(s)-alanine (1.649 g, 5.76 mmol), camptothecin (1 g, 2.88 mmol), DMAP (105 mg, 0.864 mmol) in anhyd. methylene chloride (20 mL) was cooled to 0° C. followed by the addition of DIPC (0.71 g, 0.88 mL, 5.76 mmol). The reaction mixture was slowly allowed to come to room temperature and stirred overnight. Solid separated was filtered and the filtrate was washed with 0.1 N HCl (20 mL). Solvent was removed and the solid obtained was stirred with ether (50 mL) for 10 minutes and filtered to give a pale yellow solid (1.3 g). HPLC analysis of this material indicated two peaks corresponding to two diastereomers formed by racemization at the chiral center of the amino acid. By the ratio of these peaks, it was estimated that about 25% racemization occurred. $^1$H NMR (270 Mz, CDCl$_3$): δ8.37 (s, 1H), 8.18–8.21 (m, 1H), 7.9–7.93 (m, 1H,), 7.78–7.82 (m, 1H), 7.62–7.65 (m, 1H), 7.3 (s, 1H), 5.37–5.72 (AB q, 2H), 5.3 (s, 2 H), 5.04 (s, 1H), 4.47 (m, 1H), 2.25 (m, 2 H), 1.53 (s, 9H), 1.5 (s, 3H), 0.97 (t, 3H); $^{13}$C NMR(67.8 MHz, CDCl$_3$)δ: 171.89, 167.12, 157.34, 155.07, 152.33, 148.97, 146.41, 145.57, 130.97, 130.47, 129.79, 128.36, 128.10, 128.10, 127.92, 120.09, 96.20, 80.10, 67.06, 49.93, 49.43, 31.70, 28.41, 18.11, 7.56.

Example 2

Procedure 1

Synthesis of Camptothecin-20ester of t-Boc -(S)-alanine using DIPC/Sc(OTf)$_3$/DMAP A suspension of camptothecin (0.1 g, 0.288 mmol), scandium triflate (0.085 g, 0.173 mmol), t-Boc-(S)-alanine (0.163 g, 0.864 mmol), and DMAP (0.11 g, 0.864 mmol) in anhydrous methylene chloride (10 mL) was cooled to −8° C. in an ice-salt bath for half an hour followed by addition of DIPC (0.142 mL, 0.907 mmol) and the reaction mixture was stirred at −8° C. for half an hour and at room temperature for two hours. The reaction mixture was filtered and the filtrate was washed by 20 mL 0.1 N HCl, 20 mL 0.1 M NaHCO$_3$, and 20 mL distilled water and then was evaporated to dryness. The product was purified by recrystallization from 10 mL methanol to give pure camptothecin-20-ester of t-Boc-(L)-alanine (0.140 g, 0.271 mmol, 94%). BPLC analysis indicated about only 1% or less racemization. $^1$H NMR(270 MHz, CDCl$_3$):δ8.37 (s, 1H), 8.18–8.21 (m, 1H), 7.9–7.93 (m, 1H,), 7.78–7.82 (m, 1H), 7.62–7.65 (m, 1H), 7.3 (s, 1H), 5.37–5.72 (AB q, 2H), 5.3 (s, 2H), 5.04 (s, 1H), 4.47 (m, 1H), 2.25 (m, 2H), 1.53 (s, 9H), 1.5 (s, 3H), 0.97 (t, 3H); $^{13}$C NMR(67.8 MHz, CDCl$_3$)δ: 171.89, 167.12, 157.34, 155.07, 152.33, 148.97, 146.41, 145.57, 130.97, 130.47, 129.79, 128.36, 128.10, 128.10, 127.92, 120.09, 96.20, 80.10, 67.06, 49.93, 49.43, 31.70, 28.41, 18.11, 7.56.

Procedure 2

Synthesis of camptothecin-20-ester of t-Boc-(S)alanine (1) using Sc(OTf)$_3$/DMAP and the NHS ester of t-Boc-(S) alanine A suspension of camptothecin (0.5 g, 1.44 mmol), scandium triflate (0.425 g, 0.864 mmol), and DMAP (0.527 g, 4.32 mmol) in anhydrous methylene chloride (50 mL) was cooled to −8° C. in an ice-salt bath, followed by the addition of t-Boc-(S)-alanine N-hydroxysuccinimide ester (1.24 g, 4.32 mmol). The reaction mixture was stirred at −8° C. for 30 minutes and at room temperature for 2 hours and the solid separated was filtered. The filtrate was washed with 0.1 N HCl (50 mL), 0.1 M NaHCO$_3$ ( 50 mL), and finally with distilled water (50 mL). The solvent was dried (anhyd. MgSO$_4$) and evaporated to dryness to give a solid residue which was purified by recrystallization from methanol (70 mL) to give pure compound 1 (0.701 g, 94%). HPLC analysis indicated about 2% or less racemization. $^1$HNMR (270 MHz, CDCl$_3$):δ8.37 (s, 1H), 8.18–8.21 (m, 1H), 7.9–7.93 (m, 1H,), 7.78–7.82 (m, 1H), 7.62–7.65 (m, 1H), 7.3 (s, 1H), 5.37–5.72 (AB q, 2H), 5.3 (s, 2H), 5.04 (s, 1H), 4.47 (m, 1H), 2.25 (m, 2H), 1.53 (s, 9H), 1.5 (s, 3H), 0.97 (t, 3H); $^{13}$C NMR (67.8 MHz, CDCl$_3$)δ: 171.89, 167.12, 157.34, 155.07, 152.33, 148.97, 146.41, 145.57, 130.97, 130.47, 129.79, 128.36, 128.10, 128.10, 127.92, 120.09, 96.20, 80.10, 67.06, 49.93, 49.43, 31.70, 28.41, 18.11, 7.56.

Example 3

Attempted synthesis of camptothecin-20-ester of t-Boc-(S)-alanine (1) using only DMAP (Comparative)

A suspension of camptothecin (0.2 g, 0.576 mmol) and DMAP (0.211 g, 1.73 mmol) in anhydrous methylene chloride (15 mL) was cooled to −8° C. in an ice-salt bath followed by the addition of t-Boc-(S)-alanine N-hydroxysuccinimide ester (0.495 g, 1.73 mmol). The reaction mixture was stirred at −8° C. for 30 minutes and at room temperature for 2 hours. HPLC analysis of the reaction mixture indicated that reaction didn't occur. This result indicates that in the case of camptothecin, both the lanthanide$^{III}$ metal-based catalyst, scandium triflate and base, DMAP are required for the esterification reaction.

Example 4

Attempted synthesis of camptothecin-20-O-ester of t-Boc-(S)-alanine (1) using only Sc(OTf)$_3$ (Comparative)

A suspension of camptothecin (0.2 g, 0.576 mmol) and scandium triflate (0.170 g, 0.346 mmol) in anhydrous methylene chloride (15 mL) was cooled to −8° C. in an ice-salt bath, followed by the addition of t-Boc-(S)-alanine N-hydroxysuccinimide ester (0.495 g, 1.73 mmol). The reaction mixture was stirred at −8° C. for 30 minutes and at room temperature for 2 hours. HPLC analysis of the reaction mixture indicated that reaction didn't occur. This result also indicates that for camptothecin, the lanthanide$^{III}$ metal-based catayst and base are required for the esterification reaction.

Example 5

Synthesis of camptothecin-20-ester of t-Boc-(R)alanine (2) using DIPC/DMAP (Comparative)

A suspension of t-Boc-(R)-alanine (1.09 g, 5.76 mmol), camptothecin (1 g, 2.88 mmol), DMAP (110 mg, 0.86 mmol) in anhyd methylene chloride (20 mL) was cooled to 0° C. followed by the addition of DIPC (0.71g, 0.88 mL, 5.76 mmol). The reaction mixture was slowly allowed to come to room temperature and stirred overnight. Solid separated was filtered and the filtrate was washed with 0.1N HCl (20 mL). Solvent was evaporated under vacuum and the solid obtained was stirred with ether (50 mL) for 1.0 minutes and filtered to give a pale yellow solid (1.3 g). HPLC analysis of this material indicated two peaks corresponding to two diastereomers formed by racemization at the chiral center of the amino acid. By the ratio of these peaks it was estimated that about 40% racemization occurred when scandium triflate was omitted from the process. 1HNMR (270 MHz, CDCl$_3$):δ8.34 (s, 1H), 8.22 (d, 1H), 7.89 (d, 1H,), 7.78 (t, 1H), 7.62 (t, 1H), 7.36 (s, 1H), 5.32–5.70 (AB q, 2H), 5.23 (s, 2H), 4.98 (s, 1H), 4.51 (m, 1H), 2.16 (m, 2H), 1.52 (s, 9H), 1.49 (s, 3H), 1.00 (t, 3H); $^{13}$C NMR (67.8 MHz, CDCl$_3$)δ: 172.54, 166.88, 157.47, 154.99, 152.56, 149.17, 146.43, 146.17, 130.74, 130.36, 130.03, 128.56, 128.25, 128.05, 127.86, 120.01, 96.43, 80.02, 67.03, 49.93, 49.46, 31.87, 28.27, 18.19, 7.56.

Example 6

Procedure 1

Synthesis of Camptothecin-20-ester of t-Boc-(R-alanine using DIPC/Sc(OTf)$_3$/DMAP A suspension of camptothecin (0.05 g, 0.144 mmol), scandium triflate (0.043 g, 0.86 mmol), t-Boc-(R)-alanine (0.082 g, 0.432 mmol), and DMAP (0.055 g, 0.432 mmol) in anhydrous methylene chloride (7 mL) was cooled to −10° C. in an ice-salt bath for half an hour followed by addition of DIPC (0.071 mL, 0.454 mmol) and the reaction mixture was stirred at −10° C. for half an hour and at room temperature for two hours. The reaction mixture was filtered and the filtrate was washed by 20 mL 0.1 N HCl, 20 mL 0.1 M NaHCO$_3$, and 20 mL distilled water and then was evaporated to dryness. The product was purified by recrystallization from 5 mL methanol and 5 mL ethyl ether to give pure camptothecin-20-ester of t-Boc-(R)-alanine (0.071 g, 0.138 mmol, 96%). HPLC indicated that racemization was about 2%. $^1$H NMR (270 MHz, CDCl$_3$):δ8.34 (s, 1H), 8.22 (d, 1H), 7.89 (d, 1H,), 7.78 (t, 1H), 7.62 (t, 1H), 7.36 (s, 1H), 5.32–5.70 (AB q, 2H), 5.23 (s, 2H), 4.98 (s, 1H), 4.51 (m, 1H), 2.16 (m, 2H), 1.52 (s, 9H), 1.49 (s, 3H), 1.00 (t, 3H); $^{13}$C NMR (67.8 MHz, CDCl$_3$)δ: 172.54, 166.88, 157.47, 154.99, 152.56, 149.17, 146.43, 146.17, 130.74, 130.36, 130.03, 128.56, 128.25, 128.05, 127.86, 120.01, 96.43, 80.02, 67.03, 49.93, 49.46, 31.87, 28.27, 18.19, 7.56.

Procedure 2

Synthesis of camptothecin-20-ester of t-Boc-(R)-alanine (1) using Sc(OTf)$_3$/DMAP and the NHS ester of t-Boc-(R)-alanine A suspension of camptothecin (0.3 g, 0.863 mmol), scandium triflate (0.426 g, 0.864 mmol), and DMAP (0.317 g, 2.59 mmol) in anhydrous methylene chloride (5 mL) was cooled to −10° C. in an ice-salt bath followed by the addition of t-Boc-(R)-alanine N-hydroxysuccinimide ester (0.990 g, 3.45 mmol). The reaction mixture was stirred at −10° C. for 1 hour and at room temperature for 2 hours and the solid separated was filtered. The filtrate was washed successively with 0.1 N HCl (50 mL), 0.1 M NaHCO$_3$ (50 mL), and finally with distilled water (50 mL) and dried (anhyd. magnesium sulfate).The solvent is evaporated to give a solid residue which is purified by recrystallization from methanol/ether to give (2) (0.398 g, 89%). HPLC analysis indicated that racemization was about 2%. $^1$H NMR (270 MHz, CDCl$_3$):δ8.34 (s, 1H), 8.22 (d, 1H), 7.89 (d, 1H), 7.78 (t, 1H), 7.62 (t, 1H), 7.36 (s, 1H), 5.32–5.70 (AB q, 2H), 5.23 (s, 2H), 4.98 (s, 1H), 4.51 (m, 1H), 2.16 (m, 2H), 1.52 (s, 9H), 1.49 (s, 3H), 1.00 (t, 3H); $^{13}$C NMR (67.8 MHz, CDCl$_3$)δ: 172.54, 166.88, 157.47, 154.99, 152.56, 149.17, 146.43, 146.17, 130.74, 130.36, 130.03, 128.56, 128.25, 128.05, 127.86, 120.01, 96.43, 80.02, 67.03, 49.93, 49.46, 31.87, 28.27, 18.19, 7.56.

Example 7

Synthesis of camptothecin-20-ester of (S)-(+)-2-methyl butyric acid (3)

Step 1

A suspension of N-hydroxysuccinimide (1.15 g, 10.0 mmol), 1-(3-dimethylaminopropyl)-3-ethylcarbodiimide hydrochloride (EDC) (2.11 g, 11.0 mmol), and disiopropylethyl amine (DIEA) (0.523 mL, 3.00 mmol) in anhydrous methylene chloride (30 mL) was cooled to −8° C., followed by the addition of (S)-(+)-2-methylbutyric acid (1.00 g, 9.79 mmol). The reaction mixture was stirred at −8° C. for 1 hour and at room temperature for 20 hours. The reaction mixture was washed with 0.05 N HCl (25 mL), and distilled water (25 mL) and dried (anhyd. magnesium sulfate). Solvent was evaporated under vacuum to give pure N-hydroxy succinimide ester of (S)-(+)-2-methylbutyric acid (1.74 g, 8.58 mmol, 87%) which was used in the next step without further purification. $^1$H NMR (270 MHz, CDCl$_3$):δ2.83 (s, 4H), 2.65–2.77 (m, 1H), 1.60–1.86 (m, 2H), 1.31 (d, 3H), 1.03 (t, 3H); $^{13}$C NMR (67.8MHz, CDCl$_3$)δ: 171.58, 169.18, 38.44, 26.64, 25.49, 16.28, 11.11.

STEP 2

A suspension of the above activated ester (0.172 g, 0.864 mmol), scandium triflate (0.085 g, 0.173 mmol), and DMAP (0.106 g, 0.864 mmol) in anhydrous methylene chloride (6 mL) was cooled to −8° C., followed by the addition of camptothecin (0.100 g, 0.288 mmol). The reaction mixture was stirred at −8° C. for 2 hours and at room temperature for 20 hours. The solution was washed with 0.05 N HCl (25 mL), and distilled water (25 mL) and dried (anhyd. magnesium sulfate). The solvent was evaporated to a small volume followed by precipitation with ethyl ether to give pure compound 3 (0.091 g, 73%). The degree of racemization as determined by HPLC was estimated to be about 1%. $^1$H NMR (270 MHz, CDCl$_3$):δ8.38 (s, 1H), 8.22 (d, 1H), 7.94 (d, 1H,), 7.83 (t, 1H), 7.66 (t, 1H), 7.22 (s, 1H), 5.38–5.71 (AB q, 2H), 5.27 (s, 2H), 2.50–2.61 (m, 1H), 2.10–2.34 (m, 2H), 1.49–1.84 (m, 2H), 1.26 (d, 3H), 0.99 (t, 3H), 0.95 (t, 3H), $^{13}$C NMR (67.8 MHz, CDCl$_3$)δ: 175.25, 167.24, 157.47, 152.62, 149.18, 146.25, 130.86, 130.42, 129.92, 128.60, 128.31, 128.10, 127.87, 120.56, 95.94, 75.62, 67.07, 49.88, 40.79, 31.96, 26.40, 16.18, 11.35, 7.51.

Example 8

Synthesis of ethyl 2-hydroxy isobutyrate ester of t-Boc-(S)-alanine (4)

A suspension of t-Boc-(S)-alanine N-hydroxysuccinimide ester (1.718 g, 6.00 mmol), scandium triflate (0.590 g, 1.20 mmol), and DMAP (0.733 g, 6.00 mmol) in anhydrous methylene chloride (15 mL) was cooled to −5° C., followed by the addition of ethyl-2-hydroxy isobutyrate (0.282 mL, 2.00 mmol). The reaction mixture was stirred at −8° C. for 1 hour and at room temperature for 18 hours. The solution was washed with 0.05 N HCl (25 mL), followed by distilled water (25 mL) and dried (anhyd. magnesium sulfate). The solvent was evaporated under reduced pressure to give 4 as a gummy solid (0.52 g, 86%). $^1$H NMR (270 MHz, CDCl$_3$) :δ4.13–4.21 (q, 2H), 1.57 (d, 3H), 1.55 (s, 6 H), 1.44 (s, 9H), 1.25 (t, 3H);

Example 9

Synthesis of 1-adamantanol ester of t-Boc(S)-phenylanaline (5)

A suspension of 1-adamantanol (0.200 g, 1.31 mmol), scandium triflate (0.388 g, 0.788 mmol), and DMAP (0.482 g, 3.94 mmol) in anhydrous methylene chloride (25 mL) was cooled to −10° C., followed by addition of the N-hydroxysuccinimide ester of t-Boc(S)-phenylalanine (1.90 g g, 5.25 mmol). The reaction mixture was stirred at −10° C. for 1 hour, and at room temperature for 12 hours. The solution was washed with 0.1 N HCl (20 mL) twice, followed by distilled water (20 mL) and dried (anhyd. magnesium sulfate). The solvent was evaporated under reduced pressure and the residue obtained was purified by flash column chromatography using 0 to 5% ethyl acetate in hexane to get rid of the excess starting materials. The fractions containing product were combined and evaporated to give compound 5 as a white solid (0.474 g, 90%). $^1$H NMR (270 MHz, CDCl$_3$):δ7.16–7.29 (m, 5H), 4.95 (m, 1H), 4.45 (m, 1H,), 3.07 (m, 2H), 2.15 (m, 3H), 2.05 (m, 6H), 1.64 (m, 6H), 1.42 (s, 9H); $^{13}$C NMR (67.8 MHz, CDCl$_3$)δ: 170.56, 155.05, 136.40, 129.56, 128.28, 126.76, 82.04, 79.56, 54.80, 41.19, 38.53, 36.07, 30.81, 28.30.

Example 10
Synthesis of t-butyl ester of t-Boc-(S)(OBz)Glu (6)

A suspension of t-Boc-(S)-Glu(OBz) acid (0.337 g, 1.00 mmol), t-butanol (1.885 mL, 20 mmol), scandium triflate (0.148 g, 0.30 mmol), and DMAP (0.611 g, 5.00 mmol) in anhydrous methylene chloride (10 mL) was cooled to −10° C., followed by the addition of 1-[3-(dimethylamino) propyl-] 3-ethylcarbodiimide hydrochloride, EDC, (0.383 g, 2.00 mmol). The reaction mixture was stirred at −10° C. for 1 hour, and at room temperature for 12 hours. The solution was washed with 0.1 N HCl (3×20 mL), 0.1 M NaHCO$_3$, followed by distilled water (20 mL) and dried (anhyd. magnesium sulfate). The solvent was evaporated and the residue was purified on flash silica gel column using 0 to 5% methanol in methylene chloride. The fractions containing the product were combined and evaporated carefully to give compound 6 as a colorless volatile liquid (0.31 g, 79%). $^1$H NMR(270MHz, CDCl$_3$):δ7.35 (m, 5H), 5.12 (s, 2H), 4.30 (m, 1H), 2.46 (m, 2H), 2.20 (m, 1H), 1.90 (m, 2H), 1.46 (s, 9H), 0.43 (s, 9H); $^{13}$C NMR (67.8 MHz, CDCl$_3$)δ: 172.55, 171.63, 155.35, 135.79, 128.54, 128.23, 82.17, 80.00, 69.25, 66.44, 53.39, 30.29, 28.27, 27.96, 21.71.

Example 11
Camptothecin 20-ester of 4nitro benzoic acid(7)

A suspension of camptothecin (0.2 g, 0.576 mmol), 4-nitro benzoic acid (0.385 g, 2.30 mmol), scandium triflate (0.170 g, 0.346 mmol), and DMAP (0.211 g, 1.73 mmol) in anhydrous methylene chloride (20 mL) was cooled to −10° C., followed by the addition of 1,3-diisopropyl carbodiimide (0.379 mL, 2.42 mmol). The reaction mixture was stirred at −10° C. for 1 hour and at room temperature for 2 hours. The solution was washed with 0.1 N HCl (2×20 mL), 0.1 M NaHCO$_3$ (2×20 mL), followed by distilled water (20 mL) and dried (anhyd. magnesium sulfate). The solvent was evaporated under reduced pressure and the solid residue obtained was purified by recrystallization from methanol/ether (20 mL) to give pure compound 7 (0.27 g, 94%). $^1$H NMR (270 MHz, CDCl$_3$):δ:8.40 (s, 1), 8.32 (m, 3H), 8.13 (d, 1), 7.93 (d, 1H), 7.81 (t, 1H), 7.66 (t, 1H), 7.25 (d, 2H), 5.45–5.38 (d of d, 2H), 5.31 (s, 2H), 2.35–2.48 (m, 2H), 1.11 (t, 3H); $^{13}$C NMR (67.8 MHz, CDCl$_3$)δ: 166.94, 163.52, 157.31, 152.22, 151.07, 148.81, 146.54, 145.26, 134.05, 131.26, 130.76, 129.48, 128.44, 128.20, 123.71, 120.43, 95.65, 77.24, 67.27, 49.98, 32.00, 7.72.

Example 12
Synthesis of t-butyl chloroactate (8)
Step 1

A solution of N-hydroxysuccinimide (1.15 g, 10.0 mmol), chloroacetic acid (0.945 g, 10.0 mmol), and DMAP (0.367 g, 3.00 mmol) in anhydrous methylene chloride (30 mL) was stirred at 0° C. in an ice bath for 10 minutes followed by addition of diisopropyl carbodiimide (1.66 mL, 11.0 mmol). The reaction mixture was stirred at 0° C. 30 minutes and at room temperature for 20 hours. A solid was separated and filtered and the filtrate was washed with distilled water (25 mL) and dried over anhyd. magnesium sulfate. The solvent was evaporated to dryness to give the chloroacetic acid NHS ester, which was used in the next reaction without further purification.

Step 2

A suspension of the above ester (0.192 g, 1.00 mmol), scandium triflate (0.295 g, 0.60 mmol), and DMAP (0.367 g, 3.00 mmol) in anhydrous methylene chloride (7 mL) was cooled to 0° C., followed by the addition of t-butanol (0.094 mL, 1.00 mmol). The reaction mixture was warmed to room temperature and stirred for 24 hours. The solution was washed with 0.05 N HCl (25 mL), 0.1 N NaHCO$_3$ (25 mL), followed by distilled water (25 mL) and dried (anhyd. magnesium sulfate). The solvent was evaporated under reduced pressure to give compound 8 as an oil. (0.120 g, 80%). $^1$H NMR (270 MHz, CDCl$_3$):δ5.23 (s, 2H), 1.18 (s, 9H);

| | SUMMARY | | | | |
|---|---|---|---|---|---|
| Example | Tertiary Alcohol | Acid | Method | Yield (%) | Optical Purity[b] |
| 2 (1) | 20-(S)-camptothecin | t-Boc-(S)-ala-OSu | A | 94 | 99 |
| 2 (2) | 20-(S)-camptothecin | t-Boc-(S)-Alanine | B | 95 | 99 |
| 6 (1) | 20-(S)-camptothecin | t-Boc-(R)-Ala-OSu | A | 89 | 98 |
| 6 (2) | 20-(S)-camptothecin | t-Boc-(R)-Alanine | B | 96 | 98 |
| 7 | 20-(S)-camptothecin | (S)-(+)-2-methyl butyric acid NHS ester | A | 73 | 99 |
| 9 | adamantanol | t-Boc-Phe-OSu | A | 90 | 94 |
| 10 | t-butanol | t-Boc-(S)-Glu(OBz) | B | 79 | 95 |
| 12 | ethyl 2-hydroxyl isobutyrate | t-Boc-(S)-Ala-OSu | A | 86 | ND |

[a]Method A: 0.6 eq. Sc(OTf)$_3$, 3 eq. DMAP; Method B: 0.6 eq. Sc(OTf)$_3$, 3 eq. DMAP, 3.05 eq. DIPC or EDC. [b]Optical purity was determined by HPLC analysis using chiral Phenomenex ® Chirex column.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

What is claimed is:

1. A method of forming esters of camptothecin or camptothecin derivatives, comprising:

reacting an acyl heteroaromatic ion-based compound of the formula:

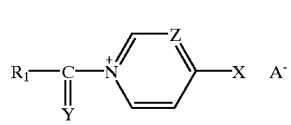

(I)

wherein

A is an anion;

R$_1$ is an aromatic or aliphatic acid residue;

Y is O or S;
Z is CH or N; and
X is selected from the group consisting of

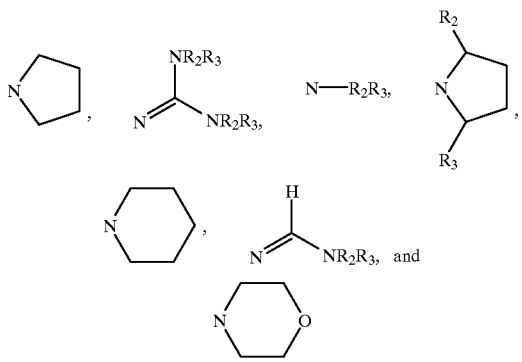

where $R_2$ and $R_3$ are independently selected from the group consisting of $C_{1-6}$ alkyls, $C_{1-6}$ substituted alkyls, $C_{3-8}$ branched alkyls, $C_{3-8}$ cycloalkyls, aryls, substituted aryls, $C_{1-6}$ alkyl aralkyls, $C_{3-8}$ branched alkyl aralkyls and $C_{3-8}$ cycloalkyl aralkyls;

with a camptothecin or camptothecin derivative in the presence of a lanthanide$^{III}$ metal-based catalyst whereby an ester of a camptothecin or camptothecia derivative is formed.

2. The method of claim 1, wherein said acyl heteroaromatic-ion based compound is formed by reacting an acylating agent with a compound of the formula

(II)

wherein
Z is CH or N; and
X is selected from the group consisting of

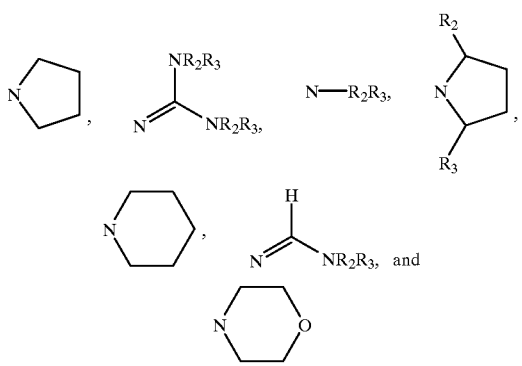

where $R_2$ and $R_3$ are independently selected from the group consisting of $C_{1-6}$ alkyls, $C_{1-6}$ substituted alkyls, $C_{3-8}$ branched alkyls, $C_{3-8}$ cycloalkyls, aryls, substituted aryls, $C_{1-6}$ alkyl aralkyls, $C_{3-8}$ branched alkyl aralkyls and $C_{3-8}$-cycloalkyl aralkyls.

3. The method of claim 2, wherein said acylating agent is selected from the group consisting of mixed anhydrides, N-hydroxy-succinimide esters, N-hydroxyphthlamide esters, active esters of carboxylic acids and acid halides.

4. The method of claim 1, wherein X is $NR_2R_3$ and Z is CH.

5. The method of claim 1, wherein said lanthanide$^{III}$ metal-based catalyst is selected from the group consisting of lanthanum, cerium, praseodymium, samarium, europium, gadolinium, terbium, dysprosium, holmium, erbium, thulium, ytterbium and lutetium-based catalysts.

6. The method of claim 1, wherein said lanthanide$^{III}$ metal-based catalyst is a scandium$^{III}$-based catalyst.

7. The method of claim 6, wherein scandium$^{III}$-based catalyst is selected from the group consisting of scandium perhaloalkylsulfonates and scandium $C_{2-12}$ alkyldifluormethyl sulfonates.

8. The method of claim 7, wherein said scandium$^{III}$-based catalyst is selected from the group consisting of scandium triflate (scandium trifluoromethanesulfonate) and scandium triflimide (scandium trifluoromethanesulfonimide).

9. The method of claim 2, wherein said acylating agent is selected from the group consisting of aliphatic and aromatic active esters of carboxylic acids.

10. The method of claim 9, wherein said aliphatic active ester of a carboxylic acid is selected from the group consisting of N-hydroxysuccinimide (NHS), N-hydroxybenzotriazole, N-hydroxyphthalimide, N-hydroxyazabenzotriazole and benzotriazol-1-yloxy-tris (dimethylamino) phosphonium hexaflurorphosphate.

11. The method of claim 9, wherein said aliphatic active ester of a carboxylic acid is a blocked amino acid active ester selected from the group consisting of S- and R-forms of alanine, leucine, isoleucine, phenylalanine, tryptophan, methionine and proline.

12. The method of claim 9, wherein said aliphatic active ester of a carboxylic acid is selected from the group consisting of 2-chloropropionic acid, 2- methylbutyric acid and substantially pure optical isomers of aliphatic active esters of carboxylic acid compounds.

13. The method of claim 2, wherein said acylating agent is a mixed anhydride selected from the group consisting of alkyl trifuloromethyl anhydrides, alkyl paranitrophenyl anhydrides.

14. The method of claim 2, wherein said acylating agent is an N-hydroxy-succinimide ester or N-hydroxyphthalimide ester.

15. The method of claim 2, wherein said acylating agent is an acid halide is selected from the group consisting of acid bromides, acid chlorides, acid fluorides and acid iodides.

16. The method of claim 1, wherein the ratio of said acyl heteroaromatic ion-based compound to said camptothecin or camptothecin derivative from about 5:1 to about 1:5.

17. The method of claim 1, wherein said lanthanide$^{III}$ metal-based catalyst is present in an amount of from about 20 to about 100 mol % based upon said acyl heteroaromatic ion-based compound.

18. The method of claim 17, wherein said lanthanide$^{III}$ metal-based catalyst is present in an amount of from about 40 to about 70 mol % based upon said acyl heteroaromatic ion-based compound.

19. The method of claim 1, wherein said reacting is carried out at a temperature of from about −20° to about 60° C.

20. A method of forming a substantially diasterioselective ester of a camptothecin or camptothecin derivative, comprising; reacting a camptothecin or camptothecin derivative with a substantially pure optical isomer of an acyl heteroaromatic ion-based compound of the formula:

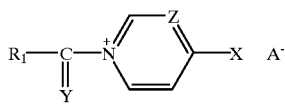
(I)

wherein
A is an anion;
R₁ is an aromatic or aliphatic acid residue;
Y is O or S;
Z is CH or N; and
X is selected from the group consisting of

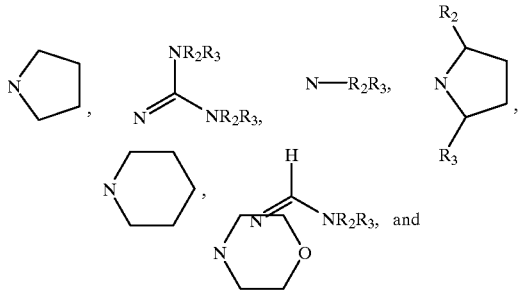

where $R_2$ and $R_3$ are independently selected from the group consisting of $C_{1-6}$ alkyls, $C_{1-6}$ substituted alkyls, $C_{3-8}$ branched alkyls, $C_{3-8}$ cycloalkyls, aryls, substituted aryls, $C_{1-6}$ alkyl aralkyls, $C_{3-8}$ branched alkyl aralkyls and $C_{3-8}$ cycloalkyl aralkyls;

in the presence of a lanthanide$^{III}$ metal-based catalyst whereby a substantially diastereoselective ester of a camptothecin or camptothecin derivative is formed.

21. The method of claim 20, wherein said acyl heteroaromatic-ion based compound is formed by reacting an acylating agent with a compound of the formula

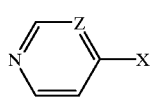
(II)

wherein
Z is CH or N; and
X is selected from the group consisting of

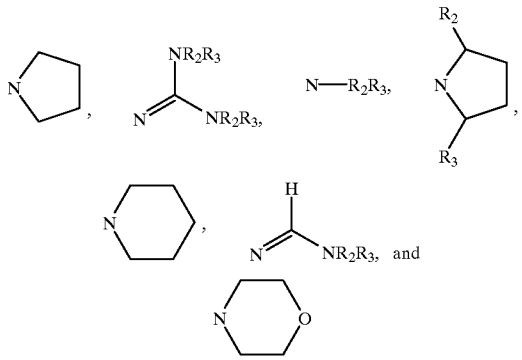

where $R_2$ and $R_3$ are independently selected from the group consisting of $C_{1-6}$ alkyls, $C_{1-6}$ substituted alkyls, $C_{3-8}$ branched alkyls, $C_{3-8}$ cycloalkyls, aryls, substituted aryls, $C_{1-6}$ alkyl aralkyls, $C_{3-8}$ branched alkyl aralkyls and $C_{3-8}$ cycloalkyl aralkyls.

22. The method of claim 21, wherein said acylating agent is selected from the group consisting of mixed anhydrides, N-hydroxy succinimide esters, N-hydroxyphthlamide esters, active esters of carboxylic acids and acid halides.

23. The method of claim 20, wherein X is $NR_2R_3$ and Z is CH.

24. The method of claim 20, wherein said lanthanide$^{III}$ metal-based catalyst is selected from the group consisting of lanthanum, cerium, praseodymium, samarium, europium, gadolinium, terbium, dysprosium, holmium, erbium, thulium, ytterbium and lutetium-based catalysts.

25. The method of claim 20, wherein said lanthanide$^{III}$ metal-based catalyst is a scandium$^{III}$-based catalyst.

26. The method of claim 25, wherein scandium$^{III}$-based catalyst is selected from the group consisting of scandium perhaloalkylsulfonates and scandium $C_{2-12}$ alkyldifluormethyl sulfonates.

27. The method of claim 26, wherein said scandium$^{III}$-based catalyst is selected from the group consisting of scandium triflate (scandium trifluoromethanesulfonate) and scandium triflimide (scandium trifluoromethanesulfonimide).

28. The method of claim 21, wherein said acylating agent is selected from the group consisting of aliphatic and aromatic esters of carboxylic acids.

29. The method of claim 28, wherein said aliphatic active ester of a carboxylic acid is selected from the group consisting of N-hydroxysuccinimide (NHS), hydroxybenzotriazole, N-hydroxyphthalimide and N-hydroxyazabenzotriazole and benzotriazol-1-yloxy-tris (dimethylamino) phosphonium hexaflurorphosphate.

30. The method of claim 28, wherein said aliphatic active ester of a carboxylic acid is a blocked amino acid active ester selected from the group consisting S- and R-forms of alanine, leucine, isoleucine, phenylalanine, tryptophan, methionine and proline.

31. The method of claim 28, wherein said aliphatic active ester of a carboxylic acid is selected from the group consisting of 2-chloropropionic acid, 2- methylbutyric acid and substantially pure optical isomers of aliphatic active esters of carboxylic acid compounds.

32. The method of claim 21, wherein said acylating agent is a mixed anhydride selected from the group consisting of alkyl trifuloromethyl anhydrides, alkyl paranitrophenyl anhydrides.

33. The method of claim 21, wherein said acylating agent is an N-hydroxy succinimide ester or an N-hydroxyphthalimide ester.

34. The method of claim 21, wherein said acylating agent is an acid halide is selected from the group consisting of acid bromides, acid chlorides, acid fluorides and acid iodides.

35. The method of claim 20, wherein the ratio of said acyl heteroaromatic ion-based compound to said camptothecin or camptothecin derivative is from about 5:1 to about 1:5.

36. The method of claim 20, wherein said lanthanide$^{III}$ metal-based catalyst is present in an amount of from about 20 to about 100 mol % based upon said acyl heteroaromatic ion-based compound.

37. The method of claim 36, wherein said lanthanide$^{III}$ metal-based catalyst is present in an amount of from about 40 to about 70 mol % based upon said acyl heteroaromatic ion-based compound.

* * * * *

UNITED STATES PATENT AND TRADEMARK OFFICE
CERTIFICATE OF CORRECTION

PATENT NO. : 6,111,107
DATED : August 29, 2000
INVENTOR(S) : Greenwald, Richard B., et al.

It is certified that error appears in the above-identified patent and that said Letters Patent is hereby corrected as shown below:

Title page,
Abstract,
Line 9, change "Z is $R_2$ N;" to -- Z is $CR_2$ or N --.

Column 1,
Line 41, change "diasteriomer" to -- diastereomer --.

Column 5,
Line 38, change "N-hydroxyphthlimide" to -- N-hydroxyphthalimide --.
Lines 54-55, change "NHS orpnitrophenyl" to -- NHS or p-nitrophenyl --.

Column 6,
Lines 23-24, change "1,(3-dimethylaminopropyl)" to -- 1-[3-(dimethyl aminopropyl)] --.
Line 30, change "(1)" to -- (I) --.
Line 34, change "(D(MAP)" to -- (DMAP) --.

Column 7,
Line 3, change "cycloakyl" to -- cycloalkyl --.
Line 19, change "derviatives" to -- derivatives --.

Column 8,
Line 67, change "tBoc" to -- t-Boc --.

Column 9,
Line 1, change "tboc" to -- t-Boc --.

Column 11,
Line 58, change "BPLC" to -- HPLC --.

Column 12,
Line 18, change "2" to -- 1 --.
Line 54, change "catayst" to -- catalyst --.
Line 58, change "t-Boc-(R) alanine" to -- t-Boc-(R)-alanine --.

UNITED STATES PATENT AND TRADEMARK OFFICE
CERTIFICATE OF CORRECTION

PATENT NO. : 6,111,107
DATED : August 29, 2000
INVENTOR(S) : Greenwald, Richard B., et al.

It is certified that error appears in the above-identified patent and that said Letters Patent is hereby corrected as shown below:

Column 13,
Line 7, change "1HNMR" to -- $^1$HNMR --.
Line 18, change "t-boc-(R-alanine" to -- t-boc-(R)-alanine--.
Line 21, change "0.86" to -- 0.086 --.

Column 14,
Line 12, delete "5".
Line 59, change "(t, 3H);" to -- -(t, 3H). --.
Line 61, change "t-Boc(S)-phenylalanine" to -- t-Boc-(S)-phenylanaline --.
Line 67, change "t-Boc(S)-phenylalanine" to -- t-Boc-(S)-phenylanaline --.

Column 15,
Line 18, change "t-Boc(S)(OBz)Glu" to -- t-Boc(S)-(OBz)-Glu --.
Line 19, change "t-Boc-(S)-Glu(OBz)" to -- t-Boc-(S)-Glu-(OBz) --.
Line 24, change "EDC, (0.383 g," to -- (EDC, 0.383 g, --.
Line 27, change "0.1 M NaHCO$_3$," to -- 0.1 M NaHCO$_3$ (2x20ml), --.
Line 40, change "4nitro benzoic acid" to -- 4-nitro benzoic acid --.
Line 54, change "(270 MHz, CDCl$_3$):δ:" to -- (270 MHz, CDCl$_3$) δ: --.
Line 63, change "Synthesis of t-butyl chloroactate" to -- Synthesis of t-butyl chlorocetate --.

Column 16,
Line 3, change "0° C. 30 minutes" to -- 0°C for 30 minutes --.

Claim 1,
Line 22 (penultimate line of claim), change "camptothecia" to -- camptothecin --.

Claim 3,
Line 3, change "hydroxy-succinimide" to -- hydroxysuccinimide --.

Claim 14,
Line 2, change "hydroxy-succinimide" to -- hydroxysuccinimide --.
Line 3, insert "an" before " N-hydroxyphthalimide".

Claim 20,
Line 1, change "diasterioselective" to -- diastereoselective --.

UNITED STATES PATENT AND TRADEMARK OFFICE
CERTIFICATE OF CORRECTION

PATENT NO. : 6,111,107
DATED : August 29, 2000
INVENTOR(S) : Greenwald, Richard B., et al.

It is certified that error appears in the above-identified patent and that said Letters Patent is hereby corrected as shown below:

Claim 20,
Lines 20-35, change " 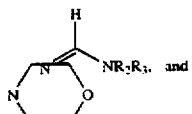 " and to 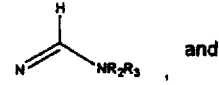 and

 --.

Claim 22,
Line 3, change "hydroxy succinimide" to -- hydroxysuccinimide --.

Claim 29,
Line 6, change "hexaflurorphosphate" to -- hexafluorophosphate --.

Claim 32,
Line 3, change "trifuloromethyl" to -- trifluoromethyl --.

Claim 33,
Line 2, change "hydroxy succinimide" to -- hydroxysuccinimide --.

Signed and Sealed this

Thirteenth Day of November, 2001

Attest:

*Nicholas P. Godici*

NICHOLAS P. GODICI
*Attesting Officer*         *Acting Director of the United States Patent and Trademark Office*

UNITED STATES PATENT AND TRADEMARK OFFICE
CERTIFICATE OF CORRECTION

PATENT NO. : 6,111,107
DATED : August 29, 2000
INVENTOR(S) : Greenwald, Richard B. et al.

It is certified that error appears in the above-identified patent and that said Letters Patent is hereby corrected as shown below:

<u>Column 15,</u>
Line 63, change "Synthesis of t-butyl chlorocetate" to
-- Synthesis of t-butyl chloroacetate --.

Signed and Sealed this

Sixth Day of August, 2002

*Attest:*

*Attesting Officer*

JAMES E. ROGAN
*Director of the United States Patent and Trademark Office*